US008730862B2

(12) United States Patent
Seok (10) Patent No.: US 8,730,862 B2
(45) Date of Patent: May 20, 2014

(54) METHOD FOR SETTING A PERIOD IN A BAN (75) Inventor: Yong Ho Seok, Anyang-si (KR)

(73) Assignee: LG Electronics Inc., Seoul (KR)

( * ) Notice: Subject to any disclaimer, the term of this patent is extended or adjusted under 35 U.S.C. 154(b) by 307 days.

(21) Appl. No.: 13/264,337

(22) PCT Filed: Apr. 14, 2010

(86) PCT No.: PCT/KR2010/002310
§ 371 (c)(1),
(2), (4) Date: Oct. 13, 2011

(87) PCT Pub. No.: WO2010/120116
PCT Pub. Date: Oct. 21, 2010

(65) Prior Publication Data
US 2012/0039215 A1 Feb. 16, 2012

Related U.S. Application Data (60) Provisional application No. 61/169,297, filed on Apr. 14, 2009.

(30) Foreign Application Priority Data

Jul. 30, 2009 (KR) .......................... 10-2009-0069997

(51) Int. Cl.
*H04H 20/71* (2008.01)
*H04W 4/00* (2009.01)
*H04J 3/00* (2006.01)
*H04L 12/28* (2006.01)
(52) U.S. Cl.
USPC ............ 370/312; 370/329; 370/336; 370/389

(58) Field of Classification Search
USPC .................................. 370/312, 329, 336, 389
See application file for complete search history.

(56) References Cited

U.S. PATENT DOCUMENTS

| 2006/0045118 | A1 | 3/2006 | Hyoung et al. | |
|---|---|---|---|---|
| 2008/0144560 | A1* | 6/2008 | Jia et al. ........................ | 370/312 |
| 2008/0228045 | A1 | 9/2008 | Gao et al. | |
| 2009/0023391 | A1 | 1/2009 | Falck | |
| 2009/0190541 | A1* | 7/2009 | Abedi ............................. | 370/329 |
| 2010/0128700 | A1* | 5/2010 | Jia et al. ........................ | 370/336 |
| 2010/0178903 | A1* | 7/2010 | Tofighbakhsh et al. ..... | 455/414.3 |
| 2010/0272076 | A1* | 10/2010 | Cavalcanti ..................... | 370/336 |

FOREIGN PATENT DOCUMENTS

KR 10-2006-0020884 A 3/2006

* cited by examiner

*Primary Examiner* — Brandon Renner
(74) *Attorney, Agent, or Firm* — Birch, Stewart, Kolasch & Birch, LLP (57) ABSTRACT A method for setting a period in a body area network (BAN) having two or more types of virtual basic service sets (BSSs) according to a type of a supported application is provided. The method includes: transmitting BAN BSS type information of a BAN BSS corresponding to an application to be supported by a device (DEV) to a central point (CP); receiving BAN BSS configuration information corresponding to the BAN BSS type information; and transmitting data to the CP in an active period according to duty cycle information included in the BAN BSS configuration information. Accordingly, the BAN BSS can be suitably managed for the application.

11 Claims, 6 Drawing Sheets

FIG. 6

METHOD FOR SETTING A PERIOD IN A BAN

CROSS REFERENCE TO RELATED APPLICATIONS

This application is a National Phase application of PCT/KR2010/002310 filed on Apr. 14, 2010, which claims the benefit under 35 U.S.C. §119(e) of U.S. Provisional Application No. 61/169,297 filed on Apr. 14, 2009 and under 35 U.S.C. §119(a) to Patent Application No. 10-2009-0069997 filed in the Republic of Korea, on Jul. 30, 2009. The entire contents of all of the above applications are hereby incorporated by reference.

TECHNICAL FIELD

The present invention relates to a wireless communication system, and more particularly, to a method for setting a period in a body area network.

BACKGROUND ART

Integrating information communication technologies into medical services or the like has drawn an increasing interest across the world. The technologies essentially include a process of measuring and transmitting bio-signals and medical information and a process of analyzing and feeding back the bio-signals and the medical information. Researches on the technologies are actively ongoing across the world. A study group called a medial wireless body area network (BAN) was created by the institute of electrical and electronics engineers (IEEE) 802.15 wireless personal area network (WPAN) standardization committee, and a task group (TG) 6 was created last year under the umbrella of the IEEE 802.15 to carry out the standardization of the BAN.

A frequency band of 402 to 405 MHz is used for a medical usage across the world. Further, an industrial, scientific and medical (ISM) band and an ultra wide-band (UWB) band also can be used in transmission of bio-signals, and thus researches thereon are actively ongoing.

A body area network (BAN) is a communication network which operates primarily near the human body. More specifically, the BAN represents a communication network and communication between devices located on, in, and off the body. The BAN can be primarily applied to a medical field, and can be further applied in various fields such as games, etc. A technology developed in association with the BAN can be applied to not only the human body but also animals or living organisms whose radio environment is similarly to that of human beings, and thus can be applied to much broader fields.

The human body is a radio communication environment which is somewhat different from a personal area network (PAN). The PAN is used to solve a communication problem that occurs between an on-body device and another device separated by 10 meters or more. Therefore, transmission through the body is not a primary target transmission environment, and a factor that obstructs the radio transmission environment caused by the human body is not much problematic.

In comparison thereto, the BAN is different in a sense that the body itself is considered as a primary radio transmission environment. Communication of the BAN may have several modes. That is, there are several types of communication modes, such as, a communication mode between in-body devices, a communication mode between an in-body device and an on-body device, a communication mode between on-body devices, a communication mode between an on-body device and an off-body device, etc.

When considering such a special radio environment and various communication modes, Bluetooth or ZigBee techniques which are conventionally developed for the PAN may be unsatisfactory, and thus there is a need to develop a signal transmission technique.

A BAN technology discussed at present can be classified into a medical BAN technology and a non-medical BAN technology in terms of an application field. In terms of a channel, the BAN technology can be classified into communication from a body surface node to a coordinator, communication between body surface nodes, communication between an in-body node and a body surface node, and a communication between in-body nodes. In addition, in terms of a medium in use, the BAN technology can be classified into a wireless scheme, a wired scheme, and a scheme of using the body itself as a medium. The BAN technology can also be classified according to whether data alone is exchanged by using a built-in power source, or power is externally supplied, or power is generated internally. In case of a BAN used for medical usage, it can be roughly classified into a wearable BAN as a network between nodes attached to the body and an implant BAN as a network between implant nodes which can be implanted in the body.

The BAN is located inside/outside of the body or on the body surface and supports low costs, low complexity, ultra-low power, and highly reliable wireless communication. In addition, the BAN supports a medical application, a non-medial application, or the like.

Herein, a medical/healthcare application uses a low data rate of below 10 Kbps and ultra-low power.

In addition, the non-medical application uses a high data rate of above 10 Mbps and low power.

As such, each application has a different requirement in terms of power and a data rate. For this, there is a need for a frame structure capable of independently serving each application.

SUMMARY OF INVENTION

According to an embodiment of the present invention, several applications are independently supported in a body area network (BAN) basic service set (BSS), and thus a transmission period suitable for each application is set. In particular, optimized BAN wireless communication is performed by performing data transmission scheduling in consideration of delay sensitivity, a property of data transmitted based on each application, or the like.

According to an aspect of the present invention, a method for setting a period in a body area network (BAN) having two or more types of virtual basic service sets (BSSs) on the basis of a type of a supported application is provided. The method includes: transmitting BAN BSS type information of a BAN BSS corresponding to an application to be supported by a device (DEV) to a central point (CP); receiving BAN BSS configuration information corresponding to the BAN BSS type information; and transmitting data to the CP in an active period according to duty cycle information included in the BAN BSS configuration information.

According to another aspect of the present invention, an apparatus for BAN wireless communication in a BAN having two or more types of virtual BSSs on the basis of a type of a supported application is provided. The apparatus includes: a radio frequency (RF) unit for receiving BAN BSS type information of a BAN BSS corresponding to an application to be supported by terminals and transmitting BAN BSS configuration information in response thereto; and a process for generating duty cycle information of a specific type of BAN BSS in accordance with the BAN BSS type information, wherein the BAN BSS configuration information includes the duty cycle information.

According to an embodiment of the present invention, a proper transmission period can be set based on a transmitted data type or application type. In particular, several applications used in a body area network (BAN) system can be independently supported. The several applications can be simultaneously supported by setting a plurality of virtual basic service sets (BSSs) in one physical BSS, and thus the same device can be more effectively used. Further, a service optimized for a desired application can be provided to terminals.

MODE FOR INVENTION

Figure 1:
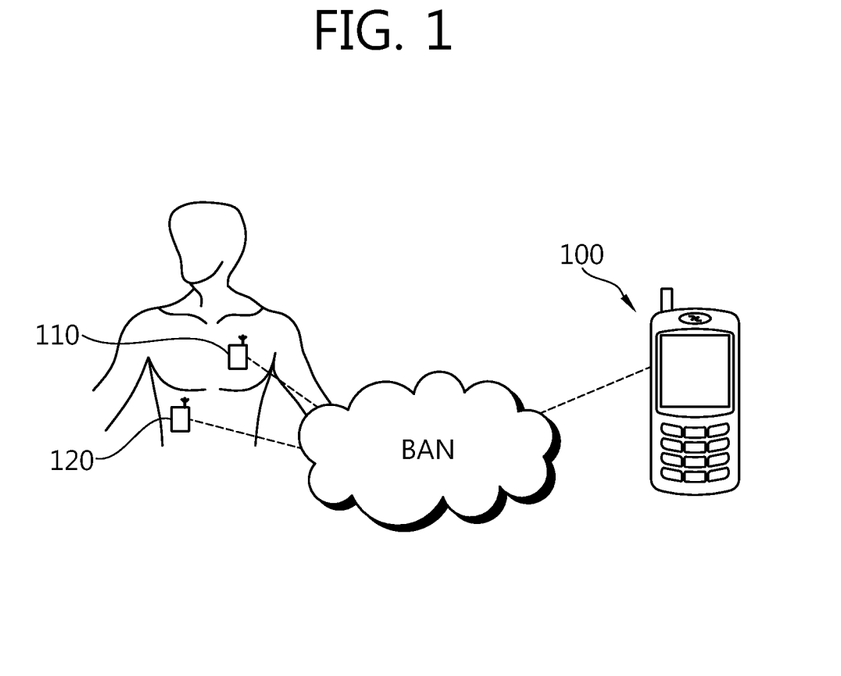
FIG. 1 shows a system configuration of a body area network (BAN)

FIG. 1 shows a system configuration of a body area network (BAN).

A BAN system may include a device which functions as a central point (CP) 100 and other terminal(s). In the BAN system, the terminals except for the CP can be simply represented by body area network devices (DEVs) 110 and 120, and can perform a function for measuring or receiving bio-signals and for delivering the bio-signals to the CP 100. Examples of the CP 100 may include a portable terminal, a mobile communication terminal, a personal digital assistant (PDA), etc. Examples of the DEVs 110 and 120 may include a bio-signal collecting device, a bio-signal measuring device, a bio-signal monitoring device, etc.

The CP 100 serves as a coordinator in the BAN system with respect to the DEVs 110 and 120. The CP 100 can receive several signals transmitted via the BAN and perform signaling processing, and then can store the signals and output the signal processing result. Further, the CP 100 can control a data transmission period, resource allocation, etc., of the DEVs 110 and 120.

Figure 2:
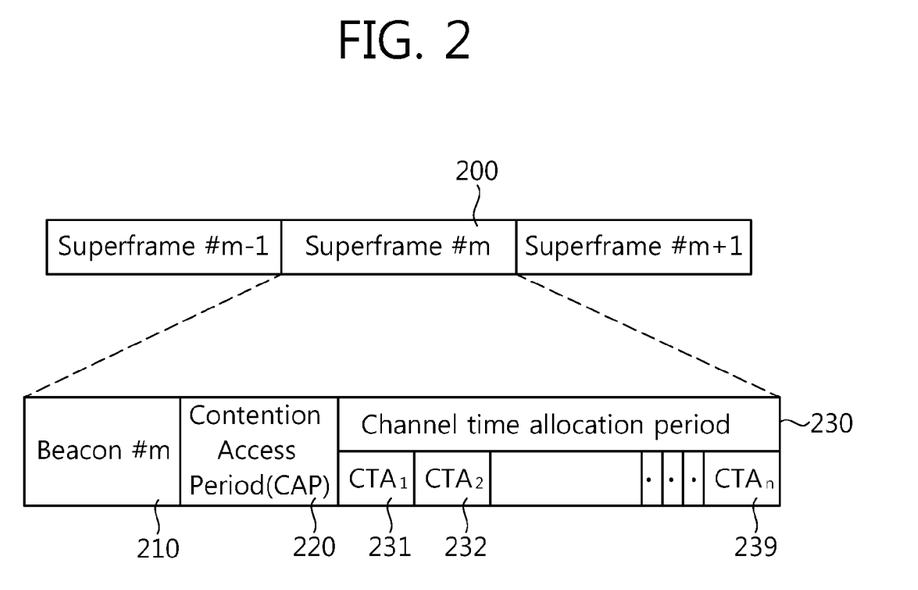
FIG. 2 shows a frame structure based on the institute of electrical and electronics engineers (IEEE) 802.15.3 standard.

FIG. 2 shows a frame structure based on the IEEE 802.15.3 standard. The IEEE 802.15.3 is a protocol for a high rate wireless personal area network (WPAN).

A full time may include several superframes. The frame structure will be described by randomly selecting a subframe #m 200 from the subframes for example. The superframe includes a beacon 210, a contention access period (CAP) 220, and a contention free period (CFP). Data transmission occurs primarily in the CFP. The CFP is indicated by a channel time allocation period (CTAP) 230. Since there is no requirement on low power in the high rate WPAN based on IEEE 802.15.3, an inactivity period is not separately defined.

The beacon frame 210 is used to transmit control information to DEVs, to allocate a radio resource in the current superframe #m 200, and to achieve time synchronization.

The CAP 220 is used for authentication, association request, association response, data stream parameter negotiation, etc. The CAP 220 uses a carrier sense multiple access/collision avoidance (CSMA/CA) mechanism for medium access.

The CTAP 230 includes one or more channel time allocations (CTAS) 231, 232, . . . , 239. The CTAP 230 may include a management CTA. The CTAS 231, 232, . . . , 239 are used for command streams, synchronous streams and asynchronous streams, or asynchronous data connections. The CTAP 230 can use a time division multiple access (TDMA) protocol when the DEVs have a specific time window.

Figure 3:
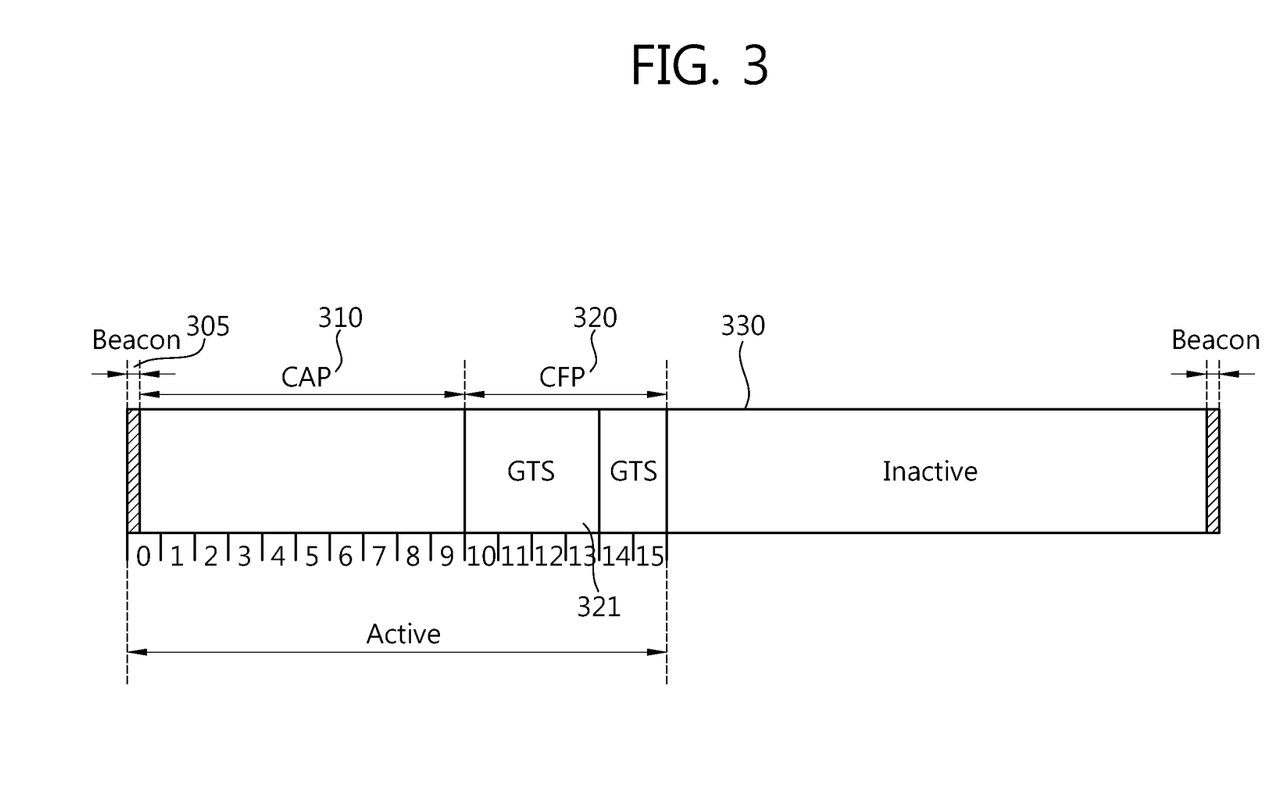
FIG. 3 shows a frame structure based on the IEEE 802.15.4 standard.

FIG. 3 shows a frame structure based on the IEEE 802.15.4 standard. The IEEE 802.15.4 is a protocol for a low rate WPAN. In the IEEE 802.15.4, a guaranteed time slot (GTS) 321 is allocated for each DEV.

A superframe is limited by a beacon 305 transmitted by a CP, and can be divided into 16 slots each of having the same size. Any DEV which intends to perform communication during a CAP 310 contends with another DEV by using the CSMA/CA mechanism.

The superframe is divided by a certain ratio into an active period and an inactive period 330. The active period includes the CAP 310 and a CFP 320. In the low rate WPAN of the IEEE 802.15.4, the active period and the inactive period 330 are divided by a certain ratio. The ratio between the active period and the inactive period 330 is referred to as a duty cycle. While the CP is within the inactive period, the CP enters a low-power mode.

That is, the active period includes the beacon 305, the CAP 310, and the CFP 320, and data transmission occurs primarily in the CFP 320. For an application having a problem of a transmission delay or an application requiring a specific data bandwidth, the CP can regulate a ratio of the active period in the superframe. The GTS 321 implies the active period assigned in this manner. The GTS 321 constitutes the CFP 320.

Figure 4:
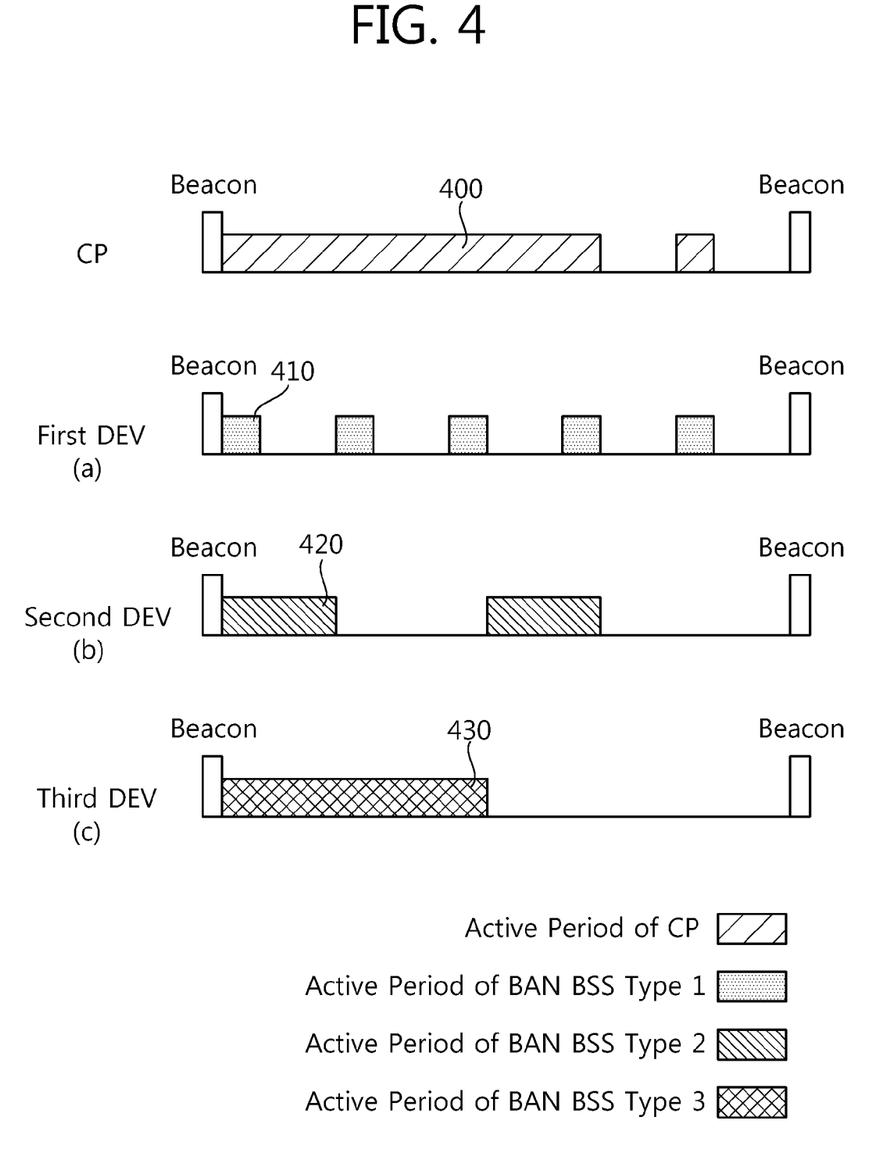
FIG. 4 shows duty cycles of a central point (CP) and devices (DEVs) supporting various BAN types according to an embodiment of the present invention.

FIG. 4 shows duty cycles of a CP and DEVs supporting various BAN types according to an embodiment of the present invention.

In the embodiment of the present invention, as a method for simultaneously supporting BAN applications having different requirements in one BAN BSS, several logical BAN BSSs or virtual BAN BSSs can be configured or set on one physical BAN. Such a BSS is hereinafter referred to as a virtual BAN.

The virtual BAN consists of a CP and DEVs. The CP can support both a medical/healthcare application and a non-medial application. Accordingly, a plurality of virtual BSSs can be configured within one physical BAN.

In general, the DEVs may not support all applications. This is because there are not many DEVs supporting both the medical/healthcare application and the non-healthcare application due to an application characteristic. However, a case where the DEVs support several applications is also included in the embodiment of the present invention.

The CP manages a BAN BSS according to a type or characteristic of applications used in the virtual BAN. BAN BSSs corresponding to respective virtual BANs define an active period and an inactive period according to a BAN application defined for each BAN BSS. That is, the BAN BSSs based on different virtual BANs can be set to have different duty cycles.

Four types of BAN BSSs are set in the present embodiment. A first BAN BSS supports a medical/healthcare application (i.e., a first application). A second BAN BSS to a fourth BAN BSS support non-medical applications. The second BAN BSS supports a real-time audio application (i.e., a second application) among the non-medical applications. The third BAN BSS supports a real-time video application (i.e., a third application) among the non-medial applications. The fourth BAN BSS supports a non-real time application (i.e., a fourth application) among the non-medical applications.

It is assumed that the CP supports only the first application, the second application, and the third application among the four types of allocations. Then, only three virtual BSSs can be managed by the CP in the BAN BSS.

A duty cycle which is set in the first BAN BSS for supporting the medical/healthcare application is indicated by (a) in FIG. 4. Then, a duty cycle related to an active period and inactive period suitable for the first application and parameters related to a contention period and contention free period in the active period are set.

The CP continuously maintains an active period 400 for a specific time period. This is because it is preferable to avoid an active period of a first DEV, a second DEV, and a third DEV and an inactive period of the CP in order to support several applications.

In the first application, i.e., the medical application, bio-signals have to be transmitted without delay and signal transmission has to be continued during a specific time period, and thus an active period 410 is repeated with a short interval. That is, in the first BAN BSS, an interval of the active period is set to be short, and a repetition frequency is significantly high.

The second application supported by the second BAN BS is the real-time audio application among the non-medical applications. The second application is an application for transmitting audio-type data on a real time basis. As indicated by (b) in FIG. 4, in the second BAN BSS, an active period 420 is longer than that of the first application, but a repetition period of the active period is set to be long. However, in comparison with another BAN BSS that transmits non-real time data, the repetition period of the active period is short, and an interval is relatively short. That is, the second DEV can transmit data during the active period 420 which is set in the second BAN BSS.

The third BAN BSS supports the third application which is the real time video application. Video data has a great data size but is less sensitive to a transmission delay in comparison with audio data or the bio-signals of the medical application. Therefore, an active period 430 is set to be long, whereas the active period 430 is not frequently repeated.

Figure 5:
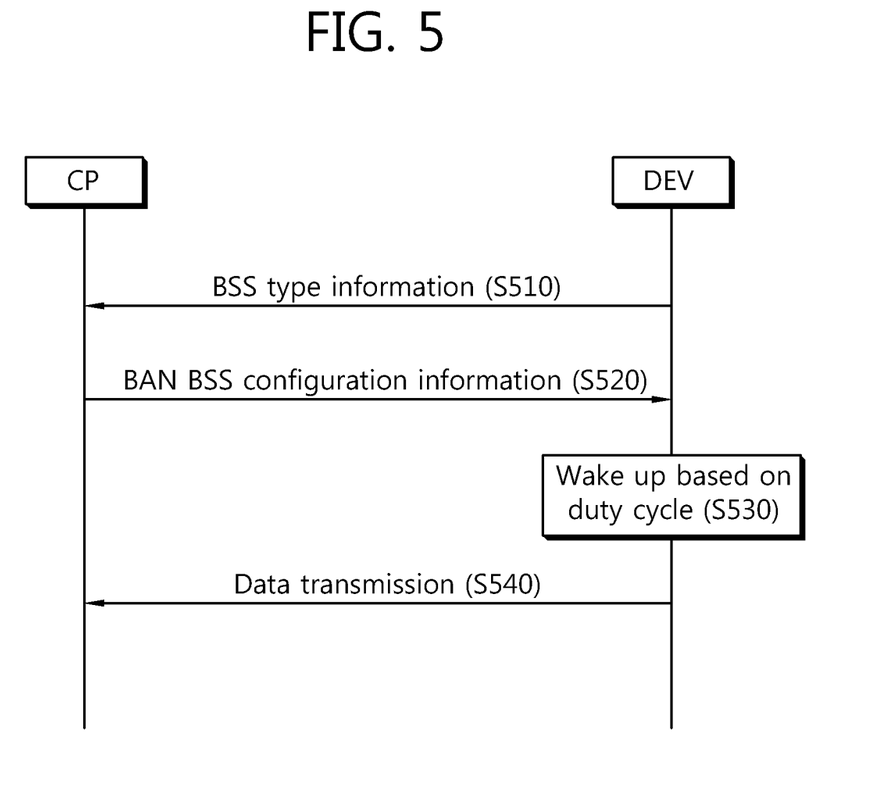
FIG. 5 is a flowchart showing a method of setting a period for each BAN type according to another embodiment of the present invention.

FIG. 5 is a flowchart showing a method of setting a period for each BAN type according to another embodiment of the present invention.

Since one CP can support several types of BAN BSSs within a virtual BAN as described above, one CP can support a first BAN BSS to a fourth BAN BSS.

A DEV transmits to-be-supported BSS type information to the CP (step S510). The BSS type information can be transmitted to the CP by being included in an association request message. The association request message is a message transmitted when the DEV intends to be associated with the CP. After receiving the association request message, the CP can transmit a response for the association request to the DEV.

Upon receiving the information on the BSS type desired by the DEV, the CP transmits BAN BSS configuration information to the DEV (step S520). The BAN BSS configuration information can be transmitted by being included in the aforementioned association response message or a beacon frame. In addition, the CP can assign a DEV identification (ID) to the DEV in this process. The DEV ID can serve as an identifier indicating which type of BSS will be supported by the DEV, and can indicate several other pieces of information corresponding to the DEV.

The DEV ID can include at least one of information indicating a specific application supported by the DEV or information indicating a specific BAN BSS type to which the DEV belongs. In addition, the DEV ID is assigned to an application supported by the DEV. In particular, in case of a DEV supporting several applications, the DEV is associated with several BAN BSSs, and in this case, a plurality of DEV IDs to be used in respective BAN BSSs can be assigned from the CP.

The BAN BSS configuration information may include not only information on an application requested to be supported by the DEV but also DEV ID information and channel bandwidth information based on a BAN BSS type of an application with a type to be supported by the DEV. This is because a type of data to be transmitted varies depending on the application type, and a channel bandwidth required for transmission of the data may also vary depending on the BAN BSS type. For example, in case of an application that transmits audio data and video data, BAN BSSs corresponding to respective applications can differently set parameter values corresponding to a channel bandwidth.

In addition thereto, transmit power information at a time of data transmission, MCS value information, or the like may be further included. In addition, BAN BSSs for respective types operate with different duty cycles according to their properties, as explained above with reference to FIG. 4. The BAN BSS configuration information may also include information on the duty cycles. For example, as described above, the more the service is sensitive to the delay, the shorter the interval of an active period of a corresponding BAN BSS is set.

In association with BSS type information received from the DEV, the CP may transmit a setting value of a parameter corresponding to each of a first BAN BSS, a second BAN BSS, a third BAN BSS, and/or a fourth BAN BSS to the DEVs irrespective of the BAN BSS configuration information. The parameter setting value or the like may be transmitted by being included in a beacon frame, an association response message, or the like.

In particular, a frame of the association request message transmitted by the DEVs to the CP to establish an association may include an additional field for a type of a BAN BSS which is intended to be associated by the DEV. The CP sends an association response frame. The aforementioned DEV ID may be included in a field of the association response frame.

Upon receiving the BAN BSS configuration information, the DEVs wake up from an active period according to a duty cycle of the configured BAN BSS (step S530), and transmit data according to a parameter which is set for a contention period and a contention free period of the active period (step S540).

However, BAN BSSs with different types may have overlapping active periods. In this case, an access priority may exist among the BAN BSSs in the contention period. For the access priority among the BAN BSSs, an arbitration inter frame space (AIFS) and a contention window are used differently in each of the BAN BSS.

The AIFS is used when all DEVs must enter an idle mode by performing carrier sensing (CS) during an AIFS time period before transmitting data in the contention period. A contention window represents a time range in which the DEVs perform backoff during any time before the DEV transmits data in the contention period.

The CP supports three BAN BSS types according to the example described above with reference to FIG. 4, and DEVs belonging to each BAN BSS type determine an active period and an inactive period according to application requirements. If a DEV belonging to a specific BAN BSS type no longer exists, the CP can terminate a service for the BAN BSS. This implies that the CP no longer has to assign an active period for the BAN BSS.

The implementation complexity, power consumption, or the like may increase in proportion to the number of BAN BSS types supported by the CP. However, in this case, there is an advantage in that a service optimized for an application required by the DEV can be provided.

Figure 6:
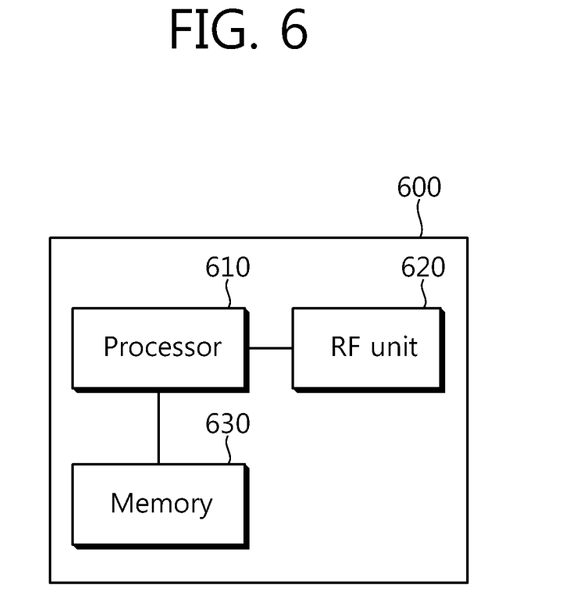
FIG. 6 is a block diagram showing a structure of a wireless communication apparatus capable of performing a method of setting a period in a BAN according to an embodiment of the present invention.

FIG. 6 is a block diagram showing a structure of a wireless communication apparatus capable of performing a method of setting a period in a BAN according to an embodiment of the present invention.

The BAN according to the embodiment of the present invention intends to support several types of applications. Therefore, several types of virtual BSSs can be set to the BAN according to an application type. In addition, a wireless communication apparatus serves as a CP in the BAN. Terminals are the aforementioned devices (DEVs) such as a biometric device, a bio-signal receiving apparatus, etc.

A BAN wireless communication apparatus includes a radio frequency (RF) unit 620 and a processor 610. The RF unit 620 performs a function of transmitting and receiving a radio signal. The processor 610 performs a function of generating a ratio signal or control information according to the embodiment of the present invention.

The apparatus may also include a memory 620 in addition to the processor 610 and the RF unit 620. The memory 630 coupled to the processor 610 stores a variety of information for driving the processor 610. The memory 630 may include a read-only memory (ROM), a random access memory (RAM), a flash memory, a memory card, a storage medium, and/or other equivalent storage devices. In addition thereto, although not shown, the wireless communication apparatus may further include a display unit or a user interface, and detailed descriptions thereof are omitted.

The processor 610 may include an application-specific integrated circuit (ASIC), a separate chipset, a logic circuit, and/or a data processing unit. The processor 610 generates a control signal or data to be transmitted to other terminals.

The RF unit 620 coupled to the processor 610 transmits radio signals generated by the processor 610, and receives radio signals transmitted by another wireless communication apparatus. The RF unit 620 may include a base-band circuit for processing radio signals. The BAN wireless communication apparatus receives BAN BSS type information of a BAN BSS corresponding to an application to be supported by terminals via the RF unit 620.

The RF unit 620 transmits BAN BSS configuration information generated by the processor on the basis of the BAN BSS type information. The BAN BSS configuration information may include duty cycle information of a corresponding type of BAN BSS.

In addition, the BAN BSS configuration information may include at least one of channel bandwidth information suitable for a corresponding application, transmit power information at a time of data transmission, and modulation and coding scheme (MCS) value information, which are generated by the processor 610 according to the BAN BSS type information. The RF unit 620 receives data from the terminals. The terminals wake up on the basis of a duty cycle, and more particularly, transmits data in a contention free period in an active period.

All functions described above may be performed by a processor such as a microprocessor, a controller, a microcontroller, and an application specific integrated circuit (ASIC) according to software or program code for performing the functions. The program code may be designed, developed, and implemented on the basis of the descriptions of the present invention, and this is well known to those skilled in the art.

While the present invention has been particularly shown and described with reference to exemplary embodiments thereof, it will be understood by those skilled in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. A method for setting a period in a body area network (BAN) having two or more types of virtual basic service sets (BSSs) according to a type of a supported application, the method comprising:
   transmitting BAN BSS type information of a BAN BSS corresponding to an application to be supported by a device (DEV) to a central point (CP);
   receiving BAN BSS configuration information corresponding to the BAN BSS type information; and
   transmitting data to the CP in an active period according to duty cycle information included in the BAN BSS configuration information.

2. The method of claim 1,
   wherein the DEV repeats the active period and an inactive period according to the duty cycle information corresponding to the BAN BSS type, and
   wherein the duty cycle information includes a ratio of the active period and the inactive period and information indicating a repetition frequency.

3. The method of claim 1, wherein the BAN BSS configuration information includes at least one of channel bandwidth information based on a specific BAN BSS type supported by the DEV, transmit power information at a time of data transmission, and modulation and coding (MCS) value information.

4. The method of claim 1, further comprising transmitting an association request message to the CP, wherein the BAN BSS type information is transmitted by being included in the association request message.

5. The method of claim 1, further comprising receiving an association response message from the CP, wherein the BAN BSS configuration information is received by being included in the association response message.

6. The method of claim 1, further comprising receiving a beacon frame from the CP, wherein the BAN BSS configuration information is received by being included in the beacon frame.

7. The method of claim 1, further comprising assigning a DEV identification (ID), wherein the DEV ID includes at least one of information regarding a specific application supported by the DEV and information regarding a specific type of the BAN BSS to which the DEV is included, and the DEV ID is assigned in accordance with the application supported by the DEV.

8. The method of claim 1,
wherein the active period includes a contention period and a contention free period, and
wherein the data is transmitted during a guaranteed time slot (GTS) assigned to each DEV during the contention free period.

9. An apparatus for BAN wireless communication in a BAN having two or more types of virtual BSSs according to a type of a supported application, the apparatus comprising:
a radio frequency (RF) unit for receiving BAN BSS type information of a BAN BSS corresponding to an application to be supported by terminals and transmitting BAN BSS configuration information in response thereto; and
a processor for generating duty cycle information of a specific type of BAN BSS in accordance with the BAN BSS type information,
wherein the BAN BSS configuration information includes the duty cycle information.

10. The apparatus of claim 9, wherein the processor generates at least one of channel bandwidth information suitable for a corresponding application, transmit power information at a time of data transmission, and MCS value information, and the BAN BSS configuration information includes at least one of the bandwidth information, the transmit power information, and the MCS information.

11. The apparatus of claim 9, wherein the RF unit receives data from the terminal that wakes up in accordance with the duty cycle.

* * * * *